United States Patent [19]
Hool et al.

[11] Patent Number: 5,542,289
[45] Date of Patent: Aug. 6, 1996

[54] APPARATUS AND METHOD FOR THE STUDY OF LIQUID-LIQUID INTERFACIAL RHEOLOGY

[75] Inventors: Kevin O. Hool; Robert C. Saunders, both of Midland, Mich.

[73] Assignee: The Dow Chemical Company, Midland, Mich.

[21] Appl. No.: 354,577

[22] Filed: Dec. 13, 1994

[51] Int. Cl.[6] .................... G01N 13/02; G01R 27/22; B01D 15/08
[52] U.S. Cl. .................... 73/64.52; 324/697; 324/691; 324/701; 73/64.55
[58] Field of Search .................... 73/64.52, 64.55; 324/697, 698, 701, 691, 693, 694

[56] References Cited

U.S. PATENT DOCUMENTS

| | | | |
|---|---|---|---|
| 4,196,615 | 4/1980 | Davis | 73/64.4 |
| 4,260,467 | 4/1981 | Smith et al. | 204/195 H |
| 4,429,273 | 1/1984 | Mazzagatti | 324/61 R |
| 4,569,226 | 2/1986 | Matteson | 73/64.4 |
| 4,650,588 | 3/1987 | Diebold | 210/656 |
| 4,846,955 | 7/1989 | Osteryoung | 204/413 |
| 4,857,829 | 8/1989 | Sagae et al. | 324/61 R |
| 5,260,667 | 11/1993 | Garcia-Golding | 324/694 |
| 5,269,176 | 12/1993 | Hool | 73/64.52 |

FOREIGN PATENT DOCUMENTS

| | | | |
|---|---|---|---|
| 0712742 | 1/1980 | U.S.S.R. | 73/64.52 |
| 0873037 | 10/1981 | U.S.S.R. | 73/64.55 |

OTHER PUBLICATIONS

H. J. Karam, "Description and Application of an Interfacial Viscometer", *Journal of Applied Polymer Science*, vol. 18, (1974) pp. 1693–1709.

C. H. Sohl, et al., "Novel technique for dynamic surface tension and viscosity measurements at liquid–gas interfaces[a]", *American Institute of Physics*, (1978) pp. 1464–1469.

H. C. Maru, et al., "Dilational Viscoelastic Properties of Fluid Interfaces–II", *Chemical Engineering Science*, vol. 34, (1979) pp. 1295–1307.

*Primary Examiner*—Hezron E. Williams
*Assistant Examiner*—David J. Wiggins

[57] ABSTRACT

The apparatus and method of the present invention relate to a novel procedure for measuring the interfacial thinning that occurs during a droplet-liquid phase coalescence event. As an example, an aqueous drop is grown at the tip of a capillary submerged into an oil phase which is layered on top of a second aqueous phase. A capillary, which is made of stainless steel, serves as one electrode while a second electrode is immersed into the second aqueous phase beneath the capillary. The oil-aqueous interface is raised to the level of the droplet until the droplet is deformed. This deformation serves as a driving force to produce thinning of the protecting interfacial film who's drainage properties govern the eventual coalescence of the water droplet into the aqueous phase. Because the interfacial film acts as a dielectric between the aqueous droplet and the second aqueous phase, an equivalent parallel plate capacitor is formed between the capillary/electrode and the second electrode immersed in the second aqueous phase. The thinning of the interfacial film is then easily measured by using an A.C. impedance measurement technique applied to the two electrodes. The change in measured capacitance is therefore directly proportional to the thinning of the interfacial film.

29 Claims, 12 Drawing Sheets

APPARATUS AND METHOD FOR THE STUDY OF LIQUID-LIQUID INTERFACIAL RHEOLOGY

BACKGROUND OF THE INVENTION

The present invention relates to the study of liquid-liquid interfacial rheology and more particularly to the study of liquid-liquid interfacial rheology through the measurement of electrical impedance across the interface.

The coalescence of liquids in suspension is known to be largely dependent upon the nature of the interfacial properties imparted to the liquid-liquid interface by the accumulation of surfactants and colloids at the interface. The interfacial properties imparted by these suspending agents serve as the foundation for the chemical industry's suspension polymerization businesses. Referring to FIG. 1, there is illustrated a dual interface between an aqueous phase 10 and an organic phase interfacial film 12 (such as oil) as may exist in a coalescence event between two aqueous droplets. A surfactant 14 has been added to the aqueous phase 10 and accumulates at the aqueous/oil interfacial boundary. The surfactant accumulates at the interfacial boundary in order to reduce the interfacial tension between the two different phases 10 and 14.

The addition of the surfactant 14 performs two basic functions in a suspension polymerization process: sizing of droplets and stabilization. The droplet sizing process of a monomer suspension results from a balance between the new surface area being formed from the breakup of droplets and the coalescence of existing droplets. The reduction of interfacial tension between the liquid phases brought about by the accumulation of the surfactant at the interface will, for any given level of work, allow for an increase in surface area (that is, smaller droplets). In order to make efficient use of the work required to produce this increased surface area, the interfacial film with the surfactant should also stabilize the suspension by preventing coalescence. There is, therefore, a need for an analytical tool that will allow this assessment of the surfactant performance characteristics at the interfacial boundary.

There have been numerous attempts made in the prior art to understand the basic mechanisms governing droplet coalescence. The most widely used approach to predict coalescence behavior in dispersed systems has been the use of single droplet coalescence experiments. In these studies, the thin films formed between the droplet and the liquid-liquid interface or between one droplet and another droplet are considered as a model for the emulsion system. For example, Hodgson, T. D. and Lee, J. C., "The Effect of Surfactants on the Coalescence of a Drop at an Interface," *J. Colloid Interfacial Sci.*, 30, (1) 1969, pp. 94–108, described an apparatus and manual technique for forming droplets and measuring coalescence times against a liquid-liquid interface. Scheele, G. E. and Leng, D. E., "An Experimental Study of Factors Which Promote Coalescence of Two Colliding Drops Suspended in Water-I," *Chem. Eng. Sci.*, 26, 1971, pp. 1867–1879, used high speed photography to study colliding droplets and presented a model to predict the coalescence behavior. Flumerfelt et al., "Magnitude and Role of Dynamic Interfacial Effects in Low Tension Flooding," *AIChE Symp. Series*, V. 78, 1982, pp. 113–126, used a modified spinning drop apparatus for droplet/droplet coalescence experiments as a basis for estimating dilational viscosity for low tension interfacial films.

A significant problem with the experiments described in the prior art is that they do not directly measure any physical properties of the draining film between the coalescing liquids. Rather, from theoretical models and measurements of physical forces (buoyancy, interfacial tension, etc.) and coalescence times, the models are used to calculate the apparent interfacial rheological figures of merit (mainly dilational viscosity and surface shear viscosity). There is therefore a need for an instrumental method that will directly measure a physical property of the draining of the interfacial film during a coalescence event. In addition, all of the prior art techniques for measurement of interfacial rheological properties are manually intensive to set up and operate, do not lend themselves to any form of automated control, and do not provide for accurate repeatability. There is, therefore, a further need for an automated system for measurement of interfacial rheological properties. The present invention is directed towards meeting these needs.

SUMMARY OF THE INVENTION

The apparatus and method of the present invention relate to a novel procedure for measuring the interfacial thinning that occurs during a droplet-liquid phase coalescence event. For example, an aqueous drop is grown at the tip of a capillary submerged into an oil phase that is layered on top of a second aqueous phase. The capillary, which is preferably made of stainless steel, serves as one electrode while a second electrode is immersed into the second aqueous phase beneath the capillary. The oil-aqueous interface is raised to the level of the droplet until the droplet is deformed. This deformation serves as a driving force to produce thinning of the protecting interfacial film surrounding the water droplet and the eventual coalescence of the water droplet into the aqueous phase. This forced thinning of the interface is governed by the rheological properties of the draining film which may be affected by the accumulation of surfactants and colloids at the interface. Characterization of the rheological properties of the interfacial film is desirable, since these properties are what principally dictate the stability of suspensions and emulsion systems. Because the interfacial film acts as a dielectric between the aqueous droplet and the second aqueous phase, the equivalent of a parallel plate capacitor is formed between the capillary/electrode and the second electrode immersed in the second aqueous phase. The thinning of the interfacial film is then easily measured by using an A.C. impedance measurement technique applied to the two electrodes. The change in measured capacitance is therefore directly proportional to the thinning of the interfacial film. When the interfacial film thins sufficiently to allow coalescence, the electrical signal is lost, evidencing the coalescence event.

In one form of the invention, a method of directly measuring interfacial rheological properties of a first fluid, comprises the steps of: (a) forming an interface between a first layer of a first fluid and a second layer of a second fluid, wherein the first and second fluids are substantially immiscible; (b) forming a drop of the second fluid within the first layer; (c) placing a first electrode in contact with the drop; (d) placing a second electrode in contact with the second layer; (e) applying voltage between the first and second electrodes, whereby the electrical equivalent of a capacitor is formed by the pendant drop, the first layer, and the second layer; (f) moving the interface toward the drop a predetermined amount; and (g) measuring the impedance between the first and second electrodes.

In another form of the invention, an apparatus for directly measuring interfacial rheological properties of a first fluid comprises a container adapted to hold a first layer of the first fluid above a second layer of the second fluid, wherein the first and second fluids are substantially immiscible and form an interface therebetween, a drop capillary having means to form a pendant drop of the second fluid and to apply an alternating current electrical signal to the pendant drop, a syringe pump operatively coupled to the drop capillary for supplying a metered quantity of the second fluid to the drop capillary, a receiving electrode adapted to receive the alternating current signal from the drop capillary, through the pendant drop, through the first layer and through the second layer, whereby an electrical equivalent of a capacitor is formed, measurement means operatively coupled to the drop capillary and the receiving electrode for measuring an impedance across the drop capillary and the receiving electrode, an analog-to-digital converter having an analog input operatively coupled to the measurement means for receipt of analog measurement data and further having a digital output, and a microprocessor operatively coupled to the syringe pump for control of the metered quantity and further coupled to the analog-to-digital converter for controlling operation of the analog-to-digital converter and for receiving digital data from the digital output.

In another form of the invention, a drop capillary adapted to form and hold a pendant drop of fluid comprises a proximal end including means for receiving a quantity of fluid and a length of hollow tubing extending from the proximal end to a distal end, the tubing having a substantially linear outside surface and a substantially linear inside surface, wherein the distance from the distal end of the outside surface to the proximal end is farther than the distance from the distal end of the inside surface to the proximal end, such that a capillary tip surface extending between the inside surface and the outside surface exhibits a frustoconical shape.

BRIEF DESCRIPTION OF THE FIGURES

The objects and features of the present invention will be readily apparent to those skilled in the art from the following description and appended drawings, illustrating embodiments of the present invention, wherein.

DESCRIPTION OF THE PREFERRED EMBODIMENTS

Figure 1:
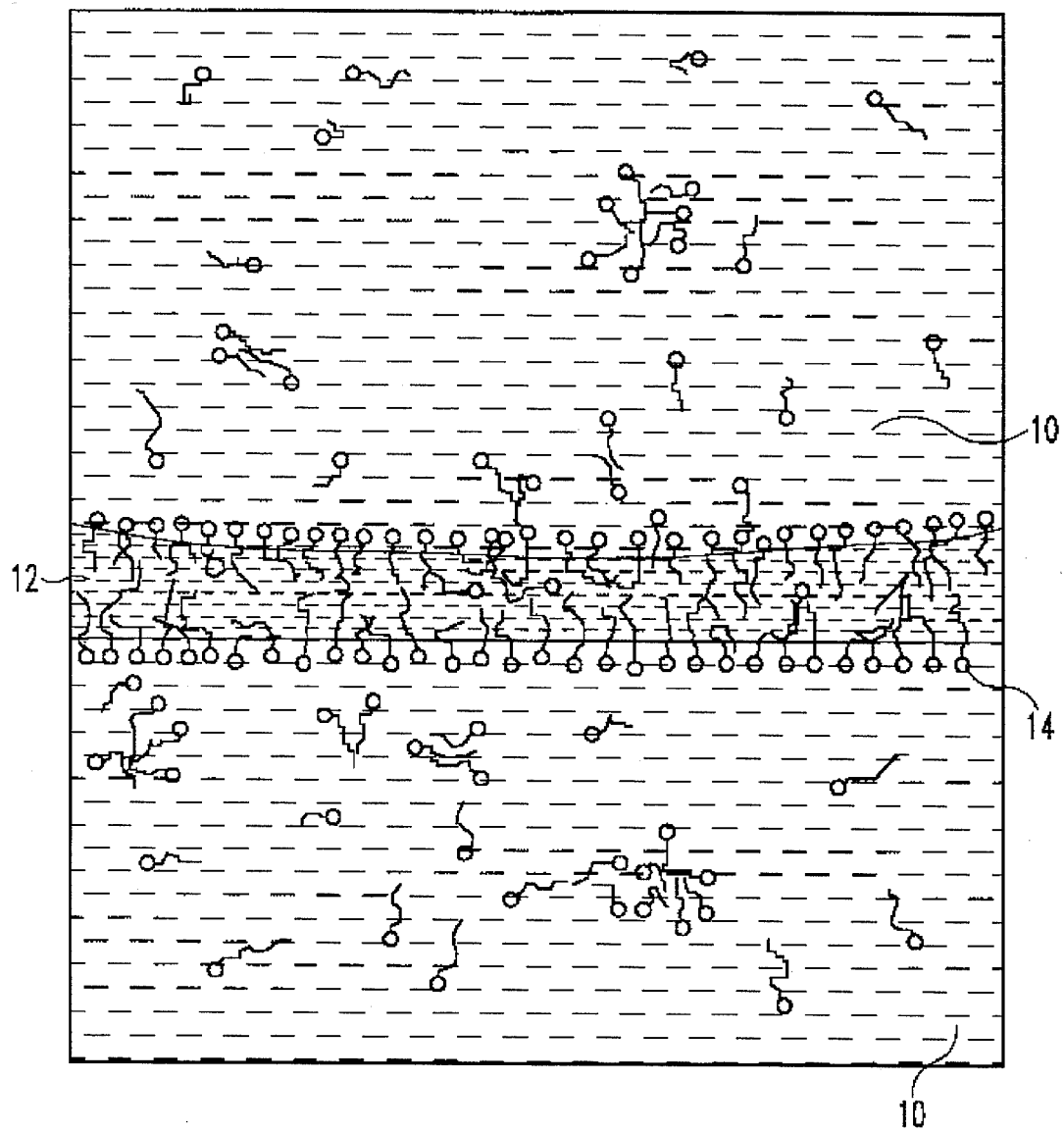
FIG. 1 is a schematic and cross-sectional view of an interface between an aqueous droplet, an oil phase, and an aqueous phase.
Figure 2A:
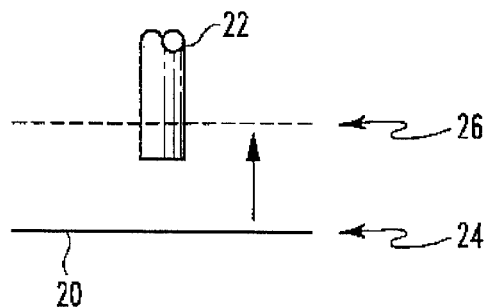
FIGS. 2a–e schematically illustrate a dynamic drop experiment of the present invention.
Figure 2B:
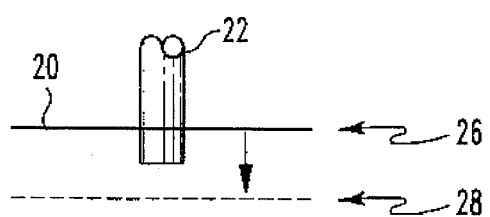
Figure 2C:
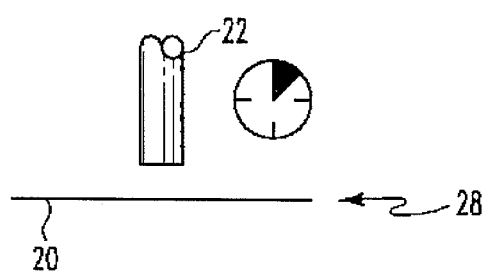
Figure 2D:
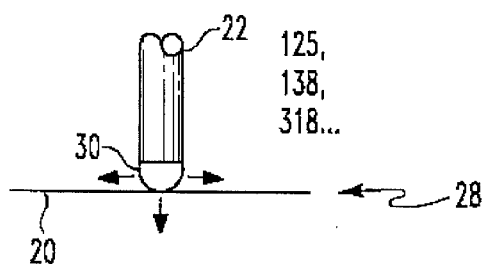
Figure 2E:
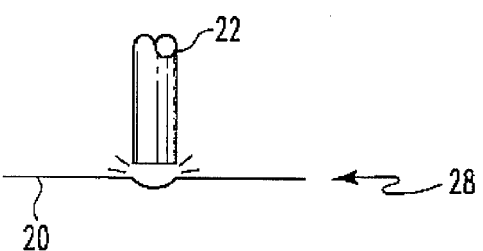
Figure 3A:
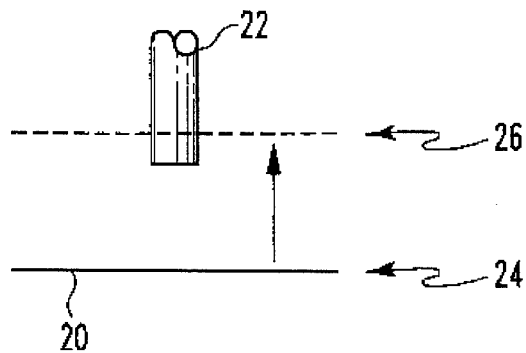
FIGS. 3a–g schematically illustrate a static drop experiment of the present invention.
Figure 3B:
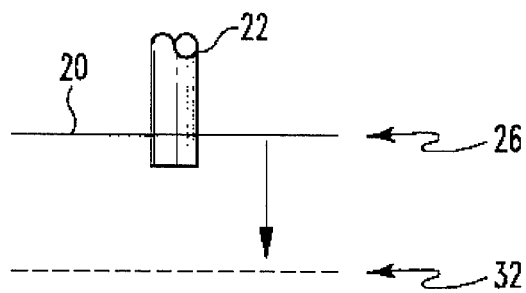
Figure 3C:
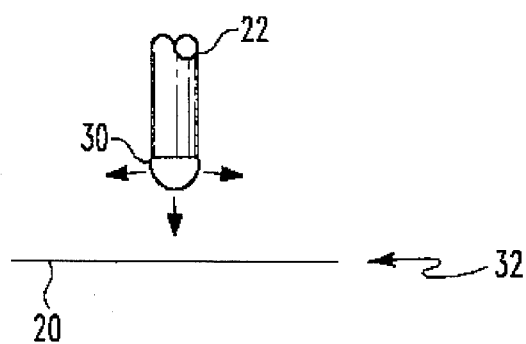
Figure 3D:
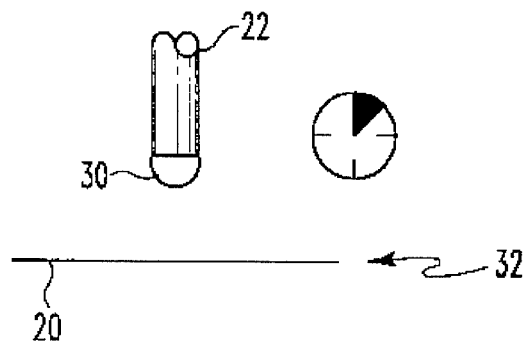
Figure 3E:
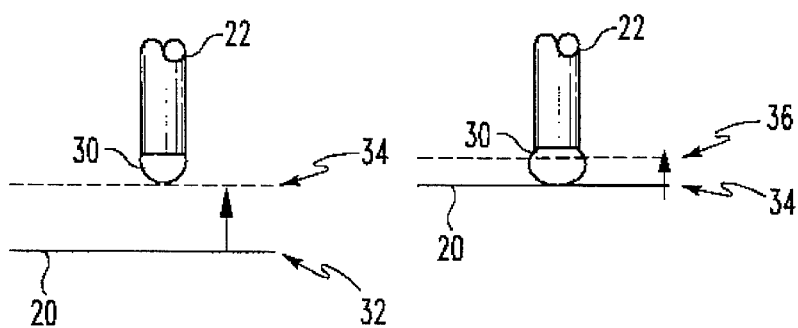
Figure 3F:
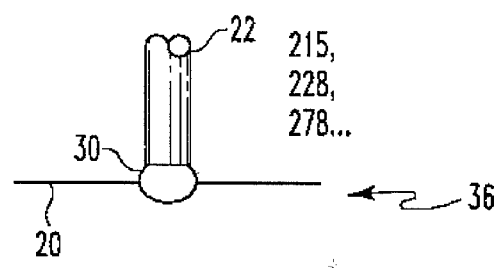
Figure 3G:
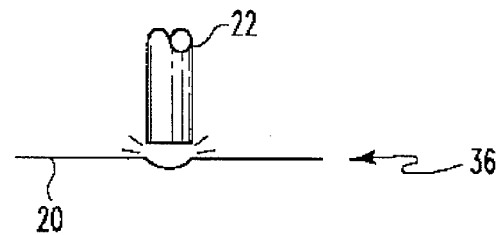
Figure 4A:
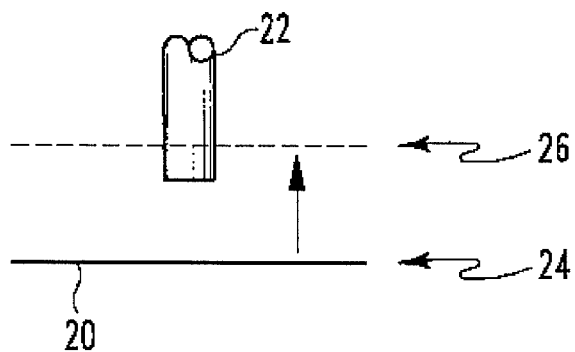
FIGS. 4a–g schematically illustrate an approach and recede experiment of the present invention.
Figure 4B:
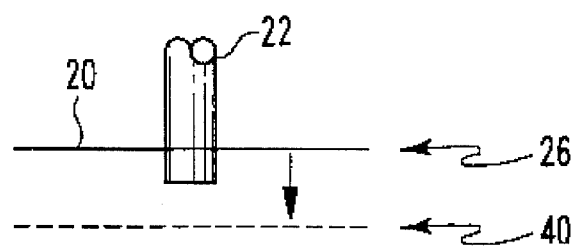
Figure 4C:
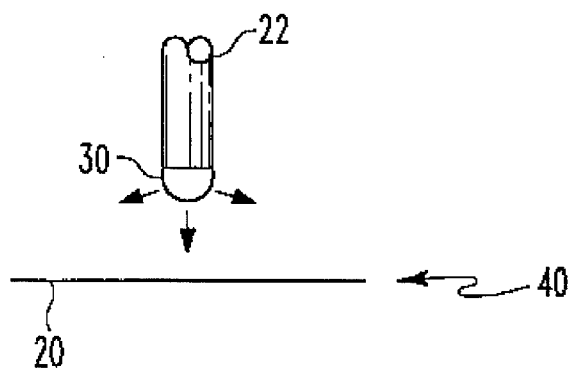
Figure 4D:
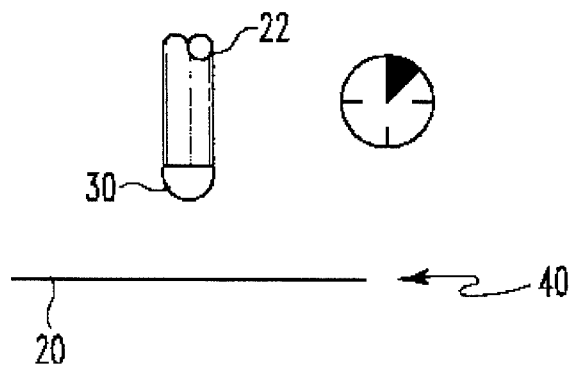
Figure 4E:
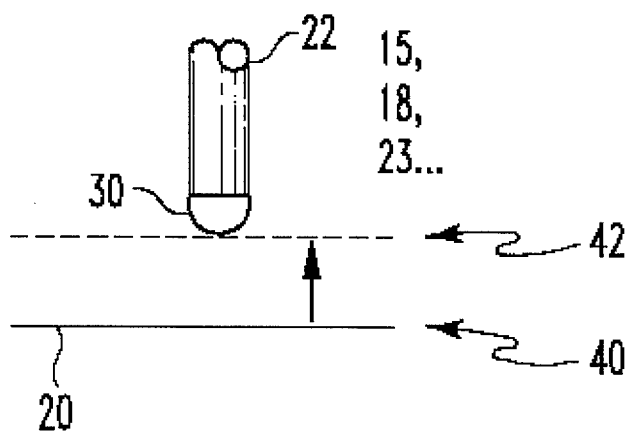
Figure 4F:
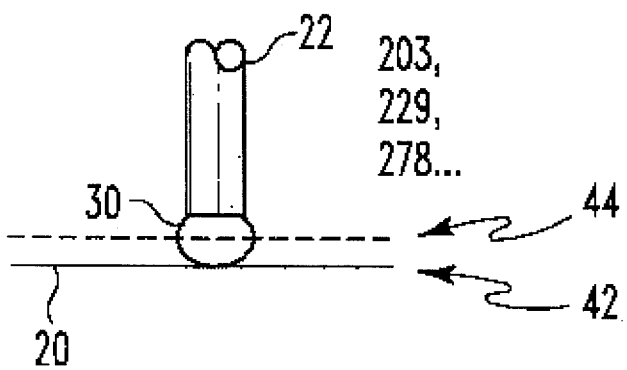
Figure 4G:
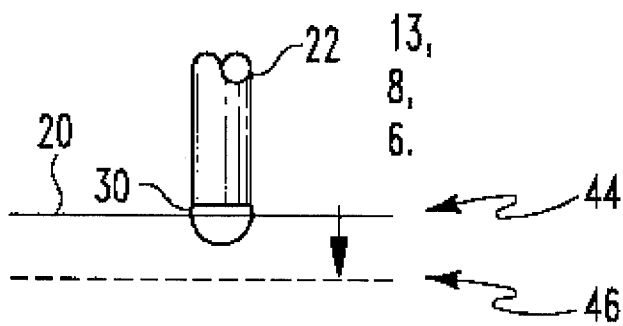

The present invention is directed towards an interfacial rheometer that records the interfacial film thinning between a pendant drop and an initially planar oil/aqueous interface that is placed in contact with the drop. The extent of contact between the droplet and the planar interface serves as the driving force for a coalescence event between the droplet and continuous aqueous phase. Such an interfacial rheometer can perform three basic types of experiments: The "Dynamic Drop" experiment, the "Static Drop" experiment, and the "Approach and Recede" experiment.

FIG. 2 illustrates the sequence of steps in the dynamic-drop experiment. In FIG. 2a, line 20 indicates the initial planar interface between an oil phase liquid above the interface 20 and an aqueous phase liquid below the interface 20. The tip of a capillary 22 is suspended in the oil phase above the interface 20. The interface 20 is then raised from its initial position 24 to the position 26, such that the bottom surface of the capillary 22 is immersed in the aqueous phase, thereby wetting capillary 22. In FIG. 2b, the interface 20 is then lowered from position 26 to a position 28 below the bottom of capillary 22. The position 28 is selected such that the interface 20 will be deformed by the pendant droplet grown on capillary 22 prior to full formation of the droplet. In FIG. 2c, the system is left in the static state for a period of time while diffusion occurs. In FIG. 2d, a pendant aqueous droplet 30 is grown from the bottom of capillary 22 such that the droplet 30 continually grows into the interface 20. The growth of the droplet 30 into the interface 20 will cause deformation of both the droplet 30 and the interface 20. As the droplet 30 grows and moves towards the interface 20, the deformation force causes the oil phase interfacial film separating the droplet 30 and the interface 20 to progressively thin. Periodic sampling of the impedance of this interfacial oil phase film is made as the droplet 30 is grown. In FIG. 2e, the interfacial film finally thins to the point where the droplet 30 coalesces with the aqueous phase. As a result, the dynamic drop experiment measures the progressive thinning of the interfacial film during drop growth or changing surface area.

Referring now to FIG. 3, there is illustrated a sequence of steps in the static drop experiment. In FIG. 3a, the interface 20 between the oil phase liquid above and the aqueous phase liquid below is raised from its starting position 24 to a position 26 above the bottom of capillary 22. This action wets the capillary 22. In FIG. 3b, interface 20 is lowered from the position 26 to a position 32. The position 32 is selected such that it will lie below a pendant droplet grown on the capillary 22 after full formation of the droplet. In FIG. 3c, a droplet 30 is grown from the bottom of capillary 22 without interaction with the interface 20. In FIG. 3d, static conditions are maintained while diffusion occurs. In FIG. 3e, the interface 20 is raised from position 32 to a position 34 such that the interface 20 is substantially at the same level as the bottom of pendant droplet 30. The interface level 34 is then further raised to position 36 such that the droplet 30 is compressed into the region of the interface 20 and deformation of both the droplet 30 and the interface 20 occurs. Data relating to the thickness of the interfacial film between pendant droplet 30 and the interface 20 is then periodically taken in FIG. 3f. In FIG. 3g, the droplet 30 finally coalesces with the aqueous phase below the interface 20 and data collection ceases. Similar to the dynamic drop experiment, the static drop experiment produces progressive thinning of the interfacial film up to coalescence, but here substantially constant drop surface area is maintained.

Referring now to FIG. 4, there is illustrated the sequence of steps in the approach and recede experiment. In FIG. 4a, the interface 20 is raised from its starting position 24 to a position 26 above the bottom of capillary 22 in order to wet the capillary 22. In FIG. 4b, the interface 20 is lowered from the position 26 to a starting position 40 below the bottom of capillary 22. The position 40 is selected such that it will lie below a pendant droplet grown on the capillary 22 after full formation of the droplet. In FIG. 4c, a pendant droplet 30 is grown from the bottom of capillary 22 without interaction with the interface 20. In step 4d, static conditions are maintained for a period of time while diffusion occurs. In step 4e, the interface 20 is raised from the position 40 to a position 42 which coincides with the bottom of the drop 30. Periodic sampling of the thickness of the interfacial film between the drop 30 and the interface 20 by impedance measurement is performed. In FIG. 4f, the interface 20 is raised further to position 44 while periodic sampling continues. In FIG. 4g, the interface 20 is lowered from position 44 to a position 46 below the bottom of drop 30 prior to the coalescence of the drop 30. In this way, data concerning the thinning of the interfacial film can be collected as well as data concerning the reformation of the interfacial film when the droplet 30 is moved away from the interface 20. The droplet does not coalesce with the aqueous phase in the approach and recede experiment.

Figure 5:
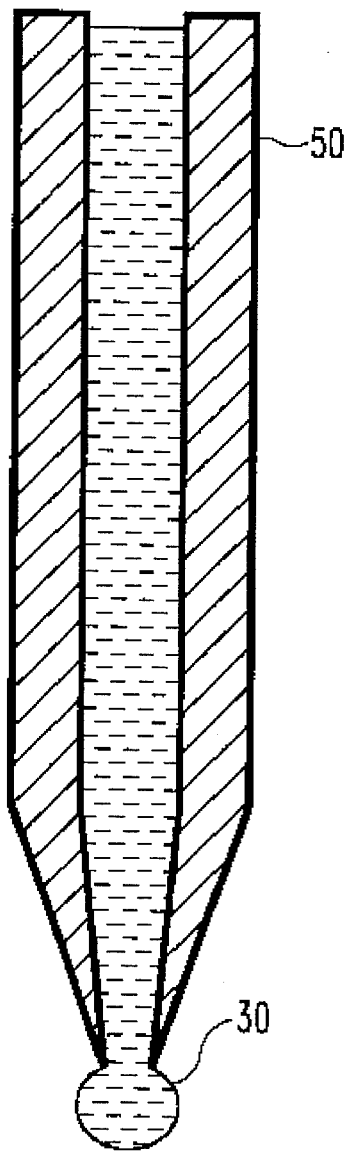
FIG. 5 is a cross-sectional view of a prior art capillary and aqueous droplet.
Figure 6:
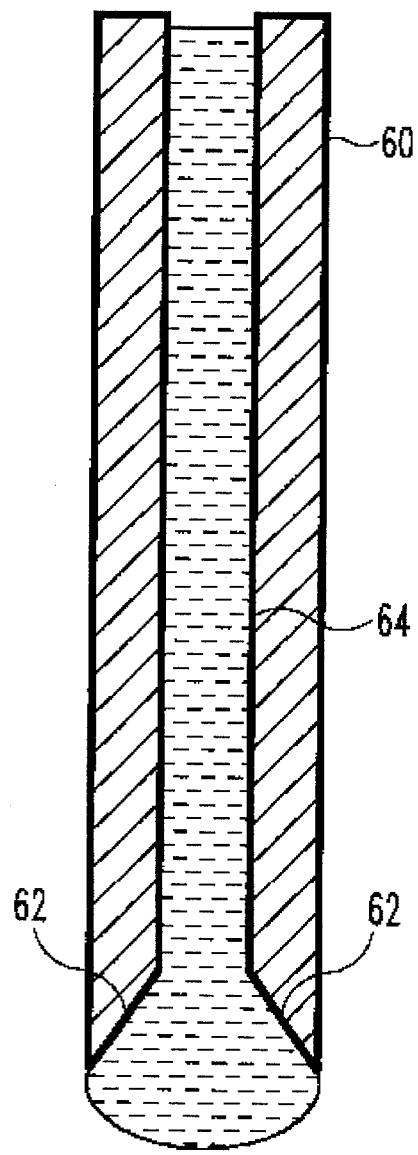
FIG. 6 is a cross-sectional view of a capillary design of the present invention.

It is desirable to have an apparatus that is capable of performing any of the three experiments illustrated in FIGS. 2–4. Additionally, it is desirable that such apparatus be able to provide some form of actual physical measurement of the thickness of the interfacial film between the droplet 30 and the interface 20 as the two are compressed and deformed together. A first step in providing such an apparatus is to design a capillary capable of supporting a pendant drop throughout these experiments. Prior art capillaries such as the capillary 50 shown in FIG. 5, have orifice geometries employing very small surface contact areas with the droplet 30 and are therefore not well suited for experiments where the droplet 30 is deformed by physical force. Under such conditions, the small surface area at the orifice contact causes the droplet 30 to be pushed off the end of the capillary 50. FIG. 6 illustrates an improved pendant drop capillary 60 of the present invention made from a 1/16" outside diameter stainless steel tube, with the orifice geometry maintained in an inverted frustoconical shape 62 leading into the narrow bore 64 of the capillary 60. In a preferred embodiment, the sides 62 of the inverted frustocone are formed at a 45 degree angle with the horizontal. The improved capillary 60 provides for a large contact area to allow for the hanging of a low tension pendant droplet. The design additionally allows for the force of deformation to be equally distributed across the large contact area between the droplet and the capillary 60. This prevents the droplet from simply being pushed off of the capillary 60 axis when the interface is raised to contact the droplet. With such a design, measurements with greater reproducibility may be obtained as compared to the prior art capillary 50.

Figure 7:
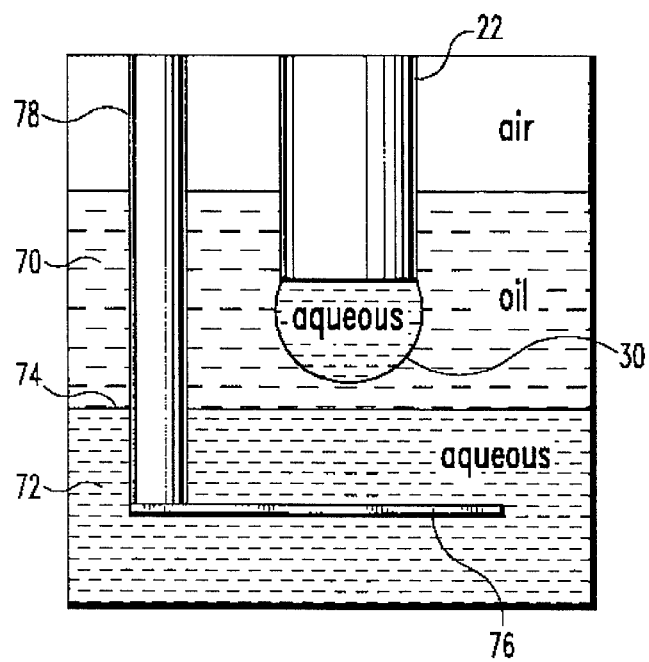
FIG. 7 is a partially sectional view of a first embodiment apparatus of the present invention.

Referring now to FIG. 7, there is shown a portion of an apparatus of the present invention, which allows direct physical measurements to be made of the thinning of an interfacial film. For the measurement of aqueous droplet systems, an organic oil phase 70 is placed over an aqueous phase 72 such that an interface 74 is formed between the two layers. It will be appreciated by those skilled in the art that the present invention is equally applicable to interfaces formed between any two substantially immiscible fluids where at least one is aqueous. As previously described for the various experiments in FIGS. 2–4, preferably a stainless steel capillary 22 is suspended into the oil phase 70 and an aqueous droplet 30 of known volume is grown from the tip of the capillary 22. A stainless steel screen electrode 76 is inserted into the lower aqueous phase 72 such that the screen electrode lies parallel to the oil-aqueous interface 74. The screen 76 is electrically coupled to an external conductor 78. The aqueous phase 72 and the aqueous droplet 30 have a small percentage of dissolved ions and therefore an electrical conductivity significantly higher than the oil phase 70. The drop must be slightly conductive, preferably 5–10 μS. Therefore, electrical current will pass through the aqueous phase 72 and the aqueous droplet 30 much more readily than through the oil phase 70. In this configuration, the droplet-oil-aqueous phase system is the electrical equivalent of a parallel plate capacitor, with the aqueous droplet 30 and the lower aqueous phase 72 acting as the effective plates of the capacitor, and the oil phase 70 acting as the dielectric of the capacitor.

Figure 8:
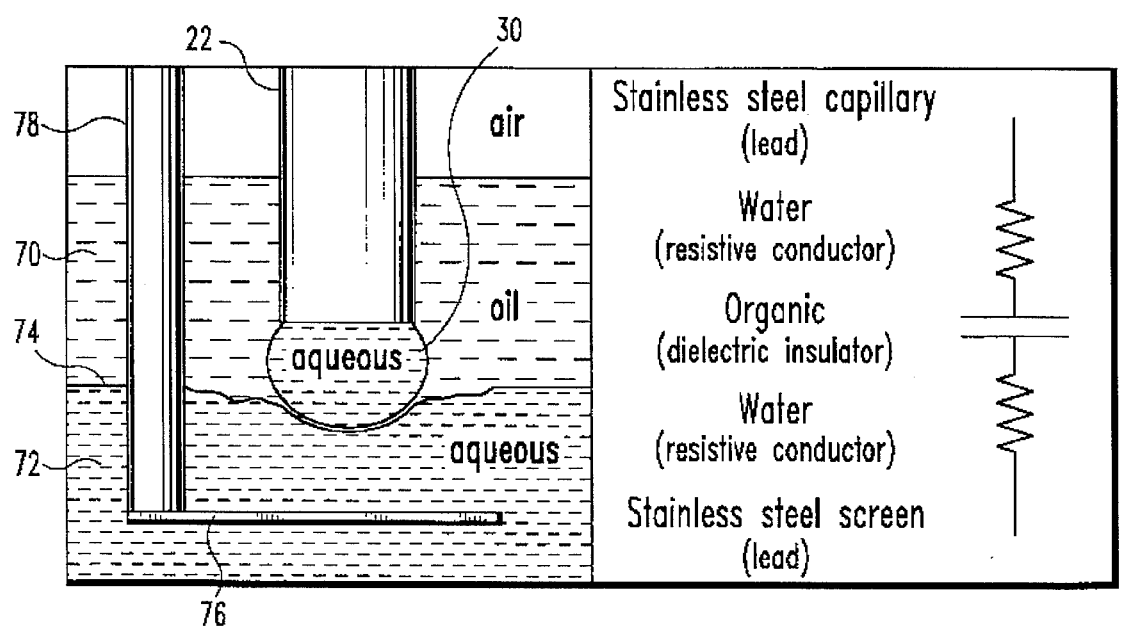
FIG. 8 is partially sectional view of the first embodiment apparatus of the present invention, including a schematic illustration and equivalent capacitance of the apparatus of the present invention.

Referring now to FIG. 8, the system of FIG. 7 is shown with the droplet 30 compressed against the interface 74, thereby deforming both the droplet 30 and the interface 74. Even in this configuration, there still exists an interfacial film of the oil phase 70 between the droplet 30 and aqueous phase 72, preventing coalescence. The equivalent electrical schematic diagram of the parallel plate capacitor arrangement formed by the droplet 30, the interfacial film of the oil phase 70 and the aqueous phase 72, is shown in FIG. 8.

The equation for the capacitance (C) of a parallel-plate capacitor is:

$$C = \frac{E_o K A}{d}$$

where $E_o$ is the permitivity of free space, K is the dielectric constant of the material separating the plates, A is the area of the plates and d is the distance between the plates. Because the planar interface 74 and the droplet 30 conform to each other when pressed together, the geometry of the system closely approximates that of a parallel-plate capacitor when the planar interface 74 and the droplet 30 are in contact. Due to the force exerted by the deformation of both the droplet 30 and the planar interface 74 when they are brought into contact, the interfacial film separating the aqueous phases thins (i.e. film drainage), reducing the distance between the effective plates, and thereby increasing the capacitance. In the apparatus of the present invention, an alternating current electrical signal of constant frequency and amplitude is transmitted from the stainless steel capillary 22 through the droplet 30 across the interface 74 to the lower aqueous layer 72, where it is conducted to the receiving screen electrode 76. The transmitted amplitude of this electrical signal is measured with respect to time. Because this measured signal is proportional to the capacitance of the system and the capacitance of the system will change as the interfacial film thins, the measured signal will provide a measure of the film thinning process leading to coalescence.

Therefore, the rate of film thinning or fluid flow from the interfacial region for a given driving force (degree of deformation) will provide information regarding the rheology of the interfacial film during the film drainage and coalescence processes. This represents a significant advantage over prior art systems that measure only the coalescence times, since knowledge of how the film thins from direct physical measurement is information that can be more significant in assessing surfactant performance than the measured coalescence times alone.

Figure 9:
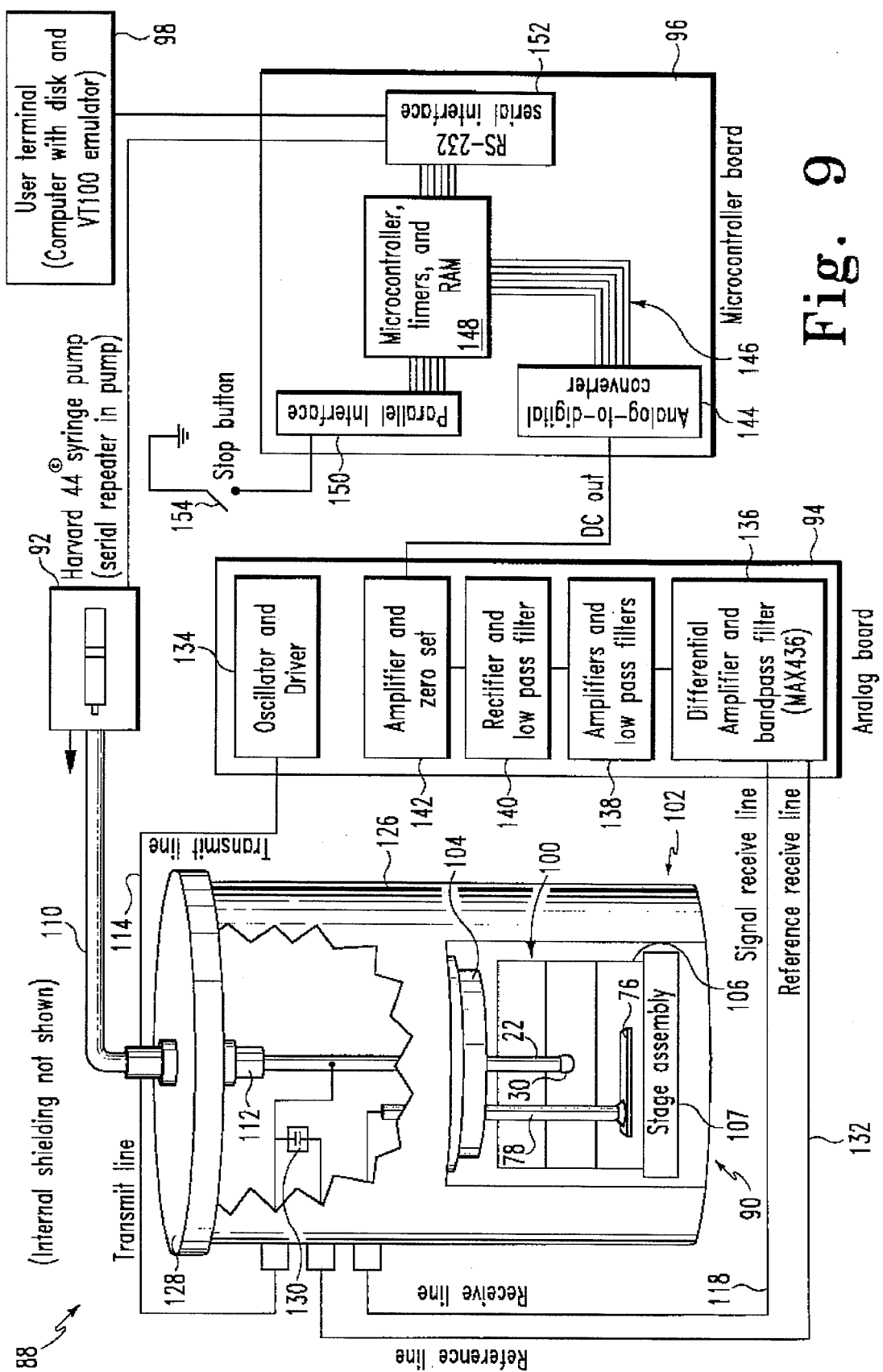
FIG. 9 is a schematic and partially sectional view of a second embodiment of the apparatus of the present invention.

A first embodiment of the full apparatus of the present invention is illustrated schematically in FIG. 9 and indicated generally at 88. The interfacial rheometer 88 is composed of five principal components: The coalescence cell 90, a precision syringe pump 92, an analog electronics signal processing board 94, a digital microcontroller 96, and a user terminal 98 with access to disk memory for data storage. The rheometer 88 utilizes a differential measurement between the capacitance of the coalescence system 90 and a reference capacitor that is mounted inside the electromagnetic shielding surrounding the coalescence cell. Such differential capacitance measurement provides additional noise immunity, which is required when using relatively high driving frequencies.

The coalescence cell structure 90 consist of a coalescence cell 100 and an electronically shielded cell housing 102. The coalescence cell 100 is comprised of a TEFLON cell cap 104 with fittings and a cylindrical borosilicate container 106. The cylinder 106 preferably has an internal diameter of 35 millimeters and an internal height of 39 millimeters; the overall height is preferably 60 millimeters. It is in the cylinder 106 where the planar oil-aqueous interface is established. The cylinder 106 sits on a precision mechanical stage assembly 107, which is under the control of the microcontroller 96 (connection not shown). The stage assembly 107 is used to raise or lower the level of the interface as required in the experiments of FIGS. 2–4. On the cell cap 104, which fits into the top of the cylinder 100, is mounted the stainless steel capillary 22 from which the pendant droplet 30 is formed. The formation of this droplet 30 is controlled by the precision syringe pump 92, wherein the aqueous fluid is pushed through 1/16 inch O.D. TEFLON tubing 110 to a fluid transfer fitting 112 located on the top of the stainless steel capillary 22. The syringe pump 92 is preferably a model Harvard 44. Coupled to the capillary 22 by a soldered connection is the transmit lead 114 from the analog board 94. Also mounted on the cell cap 104 is the stainless steel screen receiving electrode 78, which extends into the aqueous phase. The electrode 78 is electrically coupled to the electrode screen 76, which lies parallel to the interfacial boundary between the organic phase and aqueous phase. A receive line 118 couples the screen electrode 78 to the analog board 94.

The electronically shielded cell housing 102 prevents EMI/RFI interference and noise that could reduce the accuracy of the measurements being taken from the coalescence event. The housing 102 consists of a steel cylinder 126 with a removable cap 128 and an open bottom. With a preferred diameter of 105 millimeters and a preferred height of 145 millimeters, it comfortably fits over the coalescence cell 90. Located on opposing sides of the cylinder 102 are two rectangular openings which are approximately the size of the coalescence cell 90. One of these openings is visible in the view of FIG. 9. These openings are for the convenience of preparing the cell 90 and for viewing the coalescence event. The cell housing 102 is sectioned into an upper portion and a lower portion by a steel sheet (not shown) to which the coalescence cap 104 is affixed. The transmit line 114 is coupled through the upper portion of the cell housing 102 and connected to the stainless steel capillary 22 as well as to one plate of a reference capacitor 130. The other plate of reference capacitor 130 is electrically coupled through the housing 102 to a reference lead 132. The reference lead 132 couples one side of the reference capacitor 130 to the analog board 94. The upper portion of the cell housing 102 is optionally divided into three sections by three grounded flexible stainless steel screens (not shown). These screens can assist the electronic shielding of the transmit lead 114, the receive lead 118, and the reference capacitor 130 from one another, thus avoiding internal interference. However, more preferably, the transmit line 114, the receive line 118, and the reference line 132 are all shielded coaxial cables that are coupled through the cell housing 102 by means of SMA coaxial connectors and grounded to system ground.

The analog board 94 contains oscillator and driver circuits 134, which provide an alternating current electrical signal to the transmit line 114. The receive line 118 and the reference line 132 are provided as inputs to the analog board 94 and are coupled to a differential amplifier and bandpass filter circuit 136. The output of circuit 136 is provided as an input to the amplifier and low pass filter circuit 138. The signal is then provided to rectifier and low pass filter circuit 140 and then to an amplifier and zero set circuit 142. The D.C. output signal generated by the circuit 142 is coupled to an analog-to-digital converter 144, which is located on microcontroller board 96. Analog-to-digital converter 144 converts the analog D.C. signal from circuit 142 into a sampled digital signal. This sampled digital signal is supplied via parallel bus 146 to the microcontroller 148. In a preferred embodiment, the microcontroller 148 is a single chip device that contains its own RAM and associated control circuitry. However, the present invention comprehends microcontroller configurations in which the microprocessor, the memory and/or other associated control circuitry is located on separate integrated circuit chips, as is commonly known in the art. In a preferred embodiment, the microcontroller is manufactured by Z-World. The microcontroller 148 is coupled for input and output to both a parallel interface 150 and an RS-232 serial interface 152. A stop button 154 is coupled through the parallel interface 150 to the interrupt control circuitry of microcontroller 148 and is operative to stop the system when closed. The syringe pump 92 is coupled to the serial interface 152 and is thereby under the control of microcontroller 148. User terminal 98, which is preferably a personal computer with internal disk storage and a VT 100 emulator, is coupled to the RS-232 serial interface 152 for user input, data storage and display of data.

In operation, an alternating current transmit signal, preferably having a frequency of 4 MHz, is created by oscillator and drive circuitry 134 and coupled to both the capillary 22 and the reference capacitor 130 via transmit line 114. By controlling the mechanical stage 107 with microcontroller 148, the interface between the organic phase and aqueous phase may be raised and lowered, as required in the experiments illustrated in FIGS. 2–4. The syringe pump 92 is used to supply aqueous fluid to the capillary 22 in order to form pendant droplets 30 used in the experiments illustrated in FIGS. 2–4. As previously discussed, an equivalent capacitor will be formed between the capillary 22 and the electrode screen 76 as these experiments are performed. By monitoring the signal produced by the reference capacitor 130 on reference line 132, as well as the signal produced by the screen electrode 76 on receive line 118, it is possible to make a differential capacitance measurement which is proportional to the thickness of the interfacial film. During such an experiment, the transmit line 114 is continuously activated and the signals from the receive line 118 and the reference line 132 are input to the analog board 94. The circuit 136 produces a differential signal representative of the difference between the signals on lines 118 and 132 and additionally performs a bandpass filter operation on this differential signal. The circuit 138 then amplifies this filtered differential signal and performs an additional lowpass filtering operation on the signal. The output signal from circuit 138 is an alternating current signal that is applied to the rectifier circuit 140 and converted from an alternating current signal to a direct current signal. Circuit 140 additionally applies a lowpass filter to the rectified direct current signal. The output signal from circuit 140 is then applied to circuit 142, which amplifies the direct current signal and performs a zero set operation. Because the interfacial rheometer of the present invention only measures changes in capacitance, the zero set circuit 140 is used to set the initial relative capacitance reading to zero at the start of the experiment. The direct current output signal from circuit 142 is then applied to the analog-to-digital converter 144 and sampled at a fixed periodic frequency and converted into digital data. This converted digital data is supplied to microcontroller 148 and stored in memory. The digital measurement data can be displayed by the microcontroller 148 via the parallel interface 150 or the serial interface 152. This sequential relative capacitance data is proportional to the amount of thinning of the interfacial film between the droplet 30 and the organic phase-aqueous phase interface.

Figure 10:
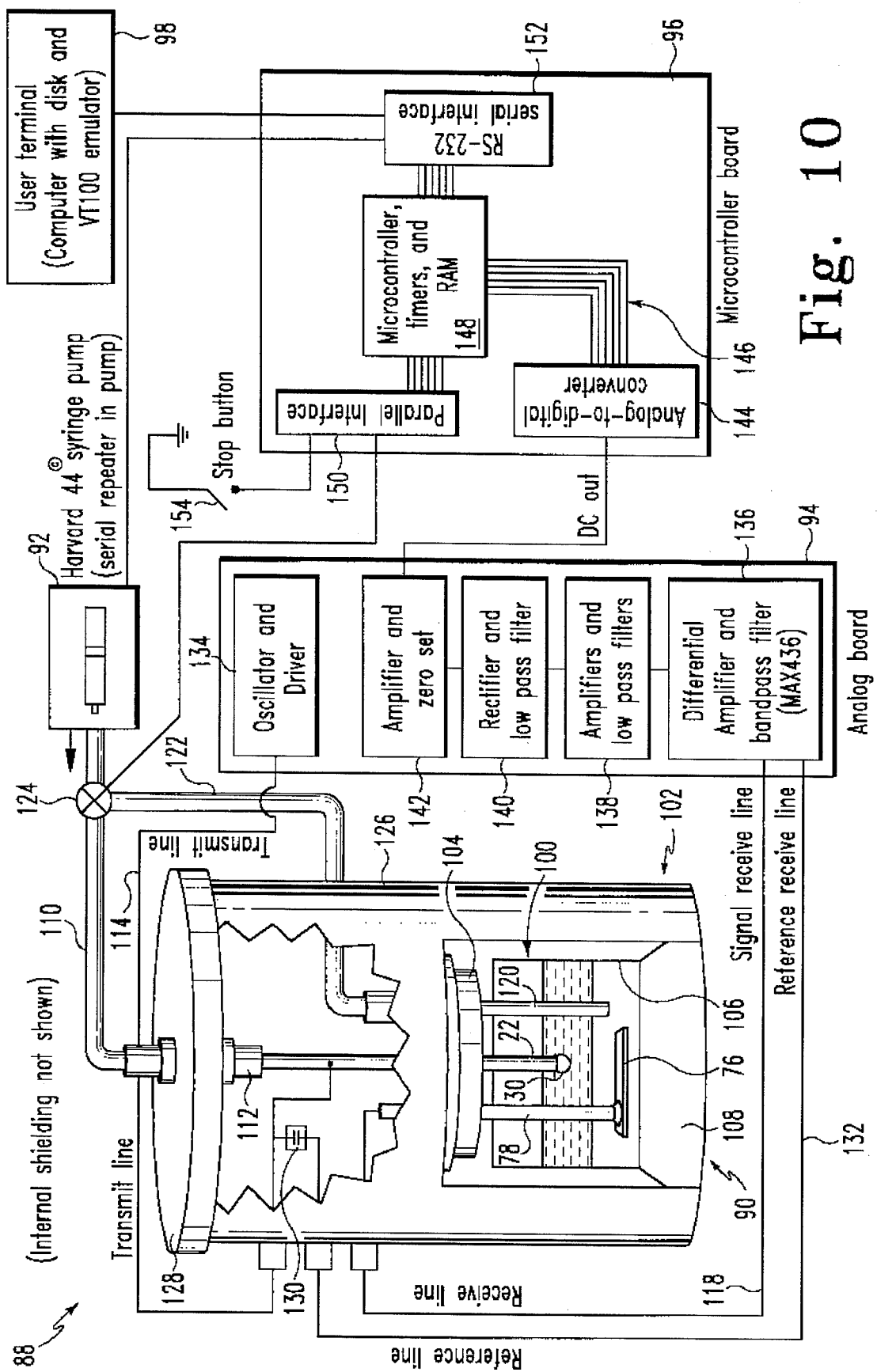
FIG. 10 is a schematic and partially sectional view of a third embodiment apparatus of the present invention.

Referring now to FIG. 10, there is illustrated a second preferred embodiment of the full apparatus of the present invention. The apparatus of FIG. 10 is substantially identical to the apparatus of FIG. 9, with the exception of the method for raising and lowering the interface. In the second embodiment of FIG. 10, the cylindrical borosilicate container 106 includes a skirted bottom 108 for stability. No mechanical stage assembly 107 is used in the second embodiment of FIG. 10. Rather, an aqueous phase infusion/extraction capillary 120 that extends into the aqueous phase is mounted in the cell cap 104. TEFLON tubing 122 couples the syringe pump 92 with the infusion/extraction capillary 120. A stopcock 124 is provided to direct the flow from the syringe pump 92 to either the tubing 110 or the tubing 122. The switching of the stopcock 124 is under the control of the microcontroller 148 through parallel interface 150. In operation, the syringe pump 92 under the control of microcontroller 148, is used to supply aqueous liquid into the infusion/extraction capillary 120. By this method, the interface between the organic phase and aqueous phase may be raised and lowered as required in the experiments illustrated in FIGS. 2–4.

Figure 11:
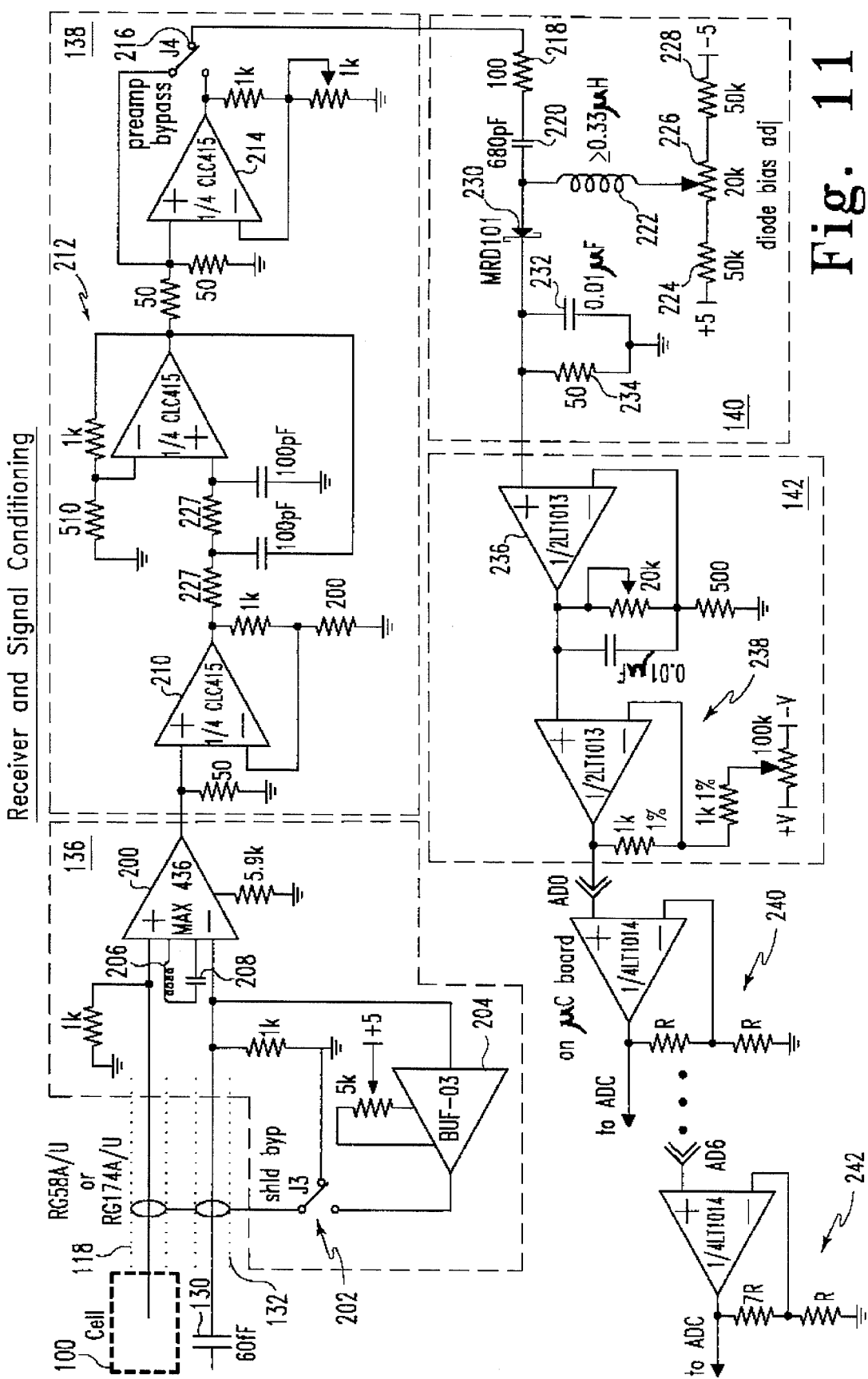
FIG. 11 is a schematic electrical diagram of the receiver and signal conditioning electronics of the present invention.

Referring now to FIG. 11, there is shown the receiver and signal conditioning portions of the analog board 94. The coalescence cell 100 is coupled to a first input of a differential amplifier 200 via the receive line 118. Differential amplifier 200 is preferably a model MAX 436, manufactured by Maxim, in Sunnyvale, Calif. The reference capacitor 130 is coupled to the other input of differential amplifier 200 via the reference line 132. The value of the reference capacitor 130 is largely dictated by the physical make-up of the coalescence cell 100. A jumper 202 is provided for connection of the coaxial shields of lines 118 and 132 to ground in the jumper position shown, or these ground shields may alternatively be driven by buffer 204 in order to minimize capacitance. The series-connected inductor 206 and capacitor 208 set the gain of the differential amplifier 200 as well as its filtering characteristics. This is due to the fact that the maximum gain of the differential amplifier is at the point of minimum impedance of the inductor 206 and capacitor 208 combination, which occurs at a resonant frequency dependent on their selected values. Alternatively, inductor 206 and capacitor 208 can be replaced with a crystal in order to set the maximum gain of differential amplifier 200 at the crystal resonant frequency. The output of the differential amplifier 200 is coupled to an input of the wide band video amplifier 210. Video amplifier 210 is preferably a model CLC 415, manufactured by Comlinear Corporation of Ft. Collins, Colo. The output of video amplifier 210 is applied to the input of a second order Sallen-Key lowpass filter 212. Another stage of amplification may be provided by wide band video amplifier 214 by selection of jumper 216. Optionally, jumper 216 many be used to bypass the amplifier 214. The signal coming from jumper 216 passes through a resistor 218, which is provided so that the video amplifier 214 (if used) does not have to drive the following capacitor 220. The capacitor 220, inductor 222, and resistors 224, 226 and 228 allow a D.C. offset to be introduced into the signal in order to adjust the bias of diode 230. Diode 230 performs the rectification of the alternating current signal in order to produce a direct current signal. Diode 230 is preferably a model MBD 301 Schottky hot carrier diode. The D.C. output from diode 230 is filtered by the capacitor 232 and resistor 234 combination. The signal is then amplified by operational amplifier 236, which is preferably a model LT 1013, manufactured by Linear Technologies of Milpitas, Calif. The output of amplifier 236 is provided to an input of the zero set circuit 238. This circuit is also based upon an operational amplifier model LT 1013. Zero set circuit 238 is necessary due to the fact that the receiver only measures the change in impedance, therefore the signal must be set to zero at the beginning of each experiment. The output of the zero set circuit, 238 is applied to each of seven analog-to-digital converter ports AD0 through AD6. Each of these analog-to-digital converter ports is coupled to the input of an amplifier circuit on the microcontroller board 96. A gain of anywhere from unity to seven is implemented by the plurality of amplifier circuits. For example, port AD0 is coupled to amplifier circuit 240, which provides a unity gain. Port AD6 is coupled to the input of amplifier circuit 242, which provides a gain of seven. The outputs of these amplifier circuits are connected to the analog-to-digital converter 144. A multiplexer (not shown) on the microcontroller board 96 selects which port channel is used as an input to the analog-to-digital connector 144. In this way, control of the gain value is in the software, which operates the multiplexer.

Figure 12:
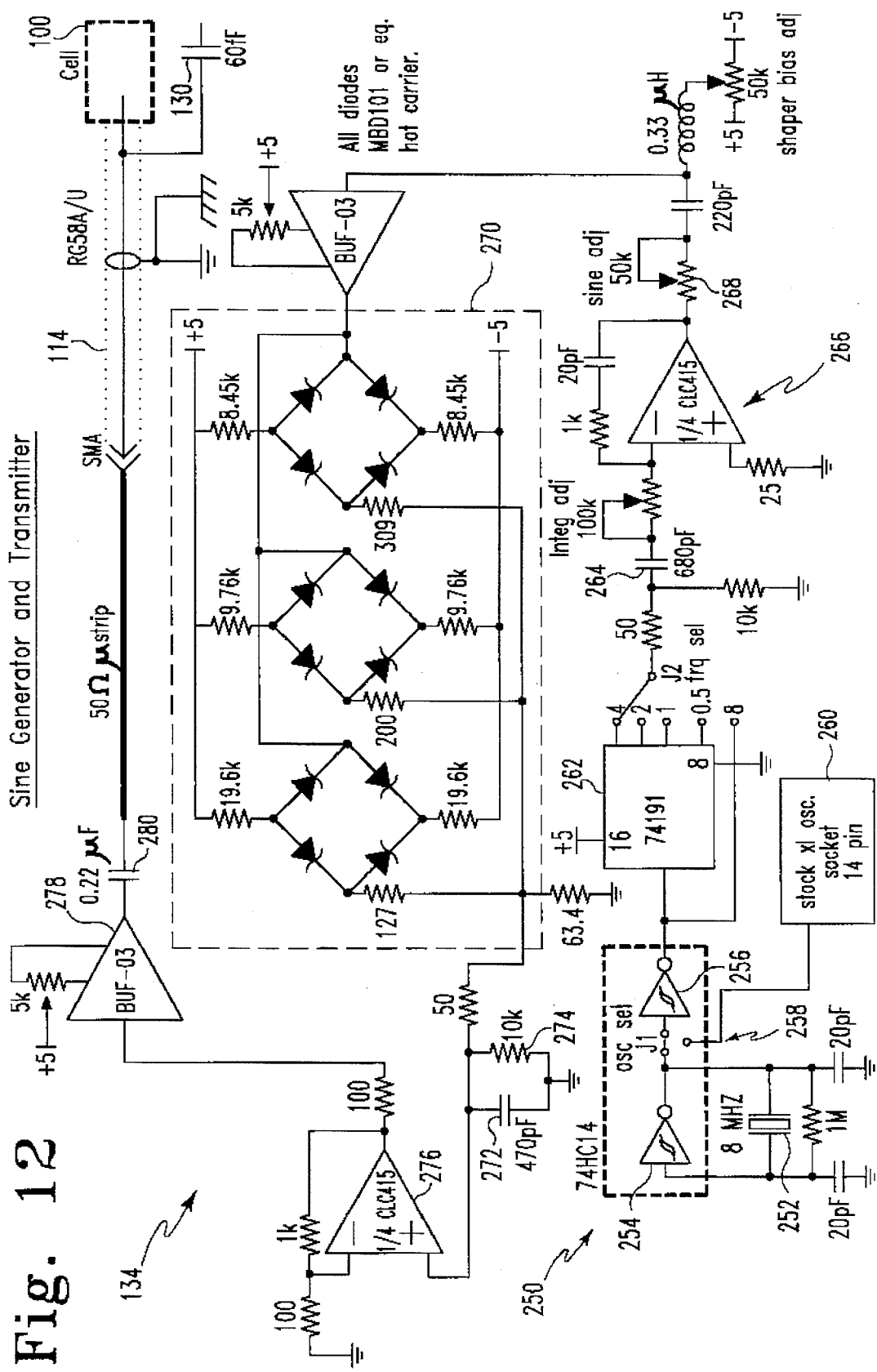
FIG. 12 is a schematic electrical diagram of the oscillator and driver circuit of the present invention.

Referring now to FIG. 12, the oscillator and driver circuit 134 is shown in greater detail. The CMOS ring oscillator 250 includes a Schmidt trigger 254 which generates a square wave output corresponding in frequency to the resonant frequency of the crystal 252. The output of Schmidt trigger 254 may be coupled to buffer 256 which is also a Schmidt trigger. The triggers 254 and 256 are preferably a model 74HC1Y, manufactured by Texas Instruments, Dallas, Tex. Alternatively, by selection of jumper 258, a prepackaged crystal oscillator 260 may be used instead of the Schmidt trigger 254 and crystal 252. The output of Schmidt trigger 256 is applied to divider 262 which allows for selection of fractional frequencies based upon the base frequency of crystal 252 (or oscillator 260). Divider 262 is preferably a model 74191, manufactured by Texas Instruments of Dallas, Tex. The output of divider 262 is applied to capacitor 264, which eliminates the D.C. component of the signal. The signal is then applied to integrator circuit 266, which transforms the square wave input signal into a triangle wave at its output by filtering the even harmonics of the input signal. Integrator 266 is based upon the same wide band video amplifier used for amplifier 210. The amplitude of the integrated output signal is adjusted by potentiometer 268. The signal is then applied to waveform shaper 270, which is comprised of an arrangement of Schottky hot carrier diodes (MBD 301). Waveform shaper 270 uses the logarithmic feature of the diodes to convert the triangle wave to a sine wave. Any glitching produced by the waveform shaper 270 is removed by the filter comprised of capacitor 272 and resistor 274. The signal is then amplified by wide band video amplifier 276, which makes up for any losses imposed on the signal in the preceding sections. Video amplifier 276 is preferably a model CLC 415. The output of amplifier 276 is applied to buffer 278, which is necessary to drive the capacitive load which follows. The buffer 278 is a BUF-03 manufactured by Analog Devices. The capacitor 280 removes any D.C. component of the sine wave signal so that no electrochemical reactions will be induced in the coalescence cell 100. The sine wave signal is applied to the coalescence cell 100 via transmit line 114.

It will be appreciated by those skilled in the art that the interfacial rheometer of the present invention provides a significant advancement in the art. The rheometer 88 allows determination of interfacial film thickness as well as rate of film drainage by direct measurement of a physical property of the interface. Moreover, the rheometer 88 provides automated control, thereby increasing its accuracy and repeatability.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method for measuring electrical impendance of a two fluid interface, which is related to or determines interfacial rheological properties of the fluid interface, comprising the steps of:
    (a) forming an interface between a first layer of a first fluid and a second layer of a second fluid, wherein the first and second fluids are substantially immiscible;
    (b) forming a drop of the second fluid within the first layer;
    (c) placing a first electrode in contact with the drop;
    (d) placing a second electrode in contact with the second layer;
    (e) applying voltage between the first and second electrodes, whereby the electrical equivalent of ac capacitor is formed by the drop, the first layer, and the second layer;
    (f) moving the interface toward the drop a predetermined amounts; and
    (g) measuring the electrical impendace between the first and second electrodes.

2. The method of claim 1, wherein the first fluid or the second fluid includes a surfactant.
3. The method of claim 1, wherein said drop is pendant.
4. The method of claim 1, wherein said drop is sessile.
5. The method of claim 1, wherein the first electrode is a capillary.
6. A method of measuring electrical impendance of a two fluid interface, which is related to or determines interfacial rheological properties of the fluid interface, comprising the steps of:
    (a) forming an interface between a first layer of a first fluid and a second layer of a second fluid, wherein the first and second fluids are substantially immiscible;
    (b) forming a drop of the second fluid within the first layer;
    (c) placing a first electrode in contact with the drop;
    (d) placing a second electrode in contact with the second layer;
    (e) applying voltage between the first and second electrodes, whereby the electrical equivalent of a capacitor is formed by the drop, the first layer, and the second layer;
    (f) growing the drop; and
    (g) measuring the electrical impedance between the first and second electrodes.

7. The method of claim 6, further comprising the step of repeating step (f) until the drop coalesces with the second layer.
8. The method of claim 6, wherein the first fluid or second fluid includes a surfactant.
9. The method of claim 6, wherein said drop is pendant.
10. The method of claim 6, wherein said drop is sessile.
11. A method of measuring electrical impendance of a two fluid interface, which is related to or determines interfacial rheological properties of the fluid interface, comprising the steps of:
    (a) forming the inteface between a first layer of a first fluid and a second layer of a second fluid, wherein the first and second fluids are substantially immiscible;
    (b) forming a drop of the second fluid within the first layer such that a portion of the first fluid remains disposed between the drop and the second layer;
    (c) placing a first electrode in contact with the drop;
    (d) placing a second electrode in contact with the second layer;
    (e) applying voltage between the first and second electrodes, whereby the electrical equivalent of a capacitor is formed by the drop, the first layer, and the second layer;
    (f) moving the interface toward the drop a first predetermined amount;
    (g) measuring the electrical impedance between the first and second electrodes; and
    (h) moving the interface away from the drop a second predetermined amount.

12. The method of claim 11, further comprising the step of repeating steps (f), (g), and (h).
13. The method of claim 11, wherein the first fluid or second fluid includes a surfactant.
14. The method of claim 11, wherein said drop is pendant.
15. The method of claim 11, wherein said drop is sessile.
16. An apparatus for directly measuring an electrical property of a two fluid interface, which is related to or determines interfacial rheological properties of the fluid interface, comprising:
    a container adapted to hold a first layer of a first fluid and a second layer of a second fluid, wherein the first and second fluids are substantially immiscible and form an interface therebetween;
    means for forming a drop of the second fluid within the first fluid;
    a first electrode adapted to contact the drop;

a second electrode adapted to contact the second layer; and means for applying voltage between said first electrode and said second electrode.

17. The apparatus of claim 16, wherein said means for forming a drop is a drop capillary.

18. The apparatus of claim 16, wherein said first electrode is a drop capillary.

19. The apparatus of claim 16, wherein said first electrode and said means for forming a drop is a drop capillary.

20. The apparatus of claim 16, further comprising: means for moving the interface relative to the drop.

21. The apparatus of claim 20, wherein the means for moving includes a precision mechanical stage mounted to the container under the interface separating the first and second layers.

22. The apparatus of claim 16, further comprising: control means operatively coupled to the drop capillary for controlling the formation of the drop.

23. The apparatus of claim 16, further comprising:

measurement means for measuring an electrical impendance between said first and second electrodes.

24. The apparatus of claim 23, wherein the measurement means includes a reference capacitor having a first plate operatively coupled to the means for applying voltage.

25. The apparatus of claim 22, further comprising:

a syringe pump operatively coupled to the drop capillary for supplying a metered quantity of the second fluid to the drop capillary, and further coupled to the control means for control of the metered quantity.

26. The apparatus of claim 16, further comprising:

a shield substantially surrounding the container and operative to block electromagnetic interference and radio frequency interference.

27. An apparatus for measuring electrical impedance of a two fluid interface, which is related to or determines interfacial rheological properties of the fluid interface;

a container adapted to hold a first layer of a first fluid and a second layer of the second fluid, wherein the first and second fluids are substantially immiscible and form an interface therebetween;

a second electrode adapted to contact the second fluid;

a drop capillary having tip at its distal end;

means for forming a drop of the second fluid at the tip of said drop capillary within said first fluid;

means for applying voltage between said drop capillary and said second electrode;

a syringe pump operatively coupled to the drop capillary for supplying a metered quantity of the second fluid to the drop capillary;

measurement means operatively coupled to he drop capillary and the second electrode for measuring an electrical impedance between the drop capillary and the second electrode;

an analog-to-digital converter having an analog input operatively coupled to the measurement means for receipt of analog measurement data and further having a digital output; and a microprocessor operatively coupled to the syringe pump for control of the metered quantity and further coupled to the analog-to-digital converter for controlling operation of the analog-to-digital converter and for receiving digital data from the digital output.

28. A drop capillary adapted to form and hold a drop of fluid due to the adhesive forces of capillary attraction between the fluid and capillary walls of a narrow capillary bore; comprising:

a distal end constructed to have a capillary tip for forming and releasing the drop; and a proximal end including means for receiving a quantity of fluid; and;

a length of hollow tubing that functions as a capillary bore, extending from the proximal end to the distal end, the tubing having s substantially linear outside surface and a substantially linear inside surface wherein the distance from the distal end of the outside surface to the proximal end is farther than the distance form the distal end of the inside surface to the proximal end, such that the capillary tip surface extending between the inside surface and the outside surface exhibits a frusto-conical shape.

29. The drop capillary of claim 28, wherein the tubing is made of an electrically conductive material.

\* \* \* \* \*